United States Patent [19]
Barnikol et al.

[11] Patent Number: 5,985,332
[45] Date of Patent: Nov. 16, 1999

[54] HEMOGLOBINS PROVIDED WITH LIGANDS PROTECTING THE OXYGEN BINDING SITES FOR USE AS ARTIFICIAL OXYGEN CARRIERS FOR DIRECT APPLICATION IN MEDICINE AND BIOLOGY, AND METHOD FOR THE PREPARATION THEREOF

[75] Inventors: Wolfgang Barnikol, Mainz; Harald Pötzschke, Wiesbaden, both of Germany

[73] Assignee: Sanguibiotech AG, Mainz, Germany

[21] Appl. No.: 09/005,093

[22] Filed: Jan. 9, 1998

[30] Foreign Application Priority Data

Jan. 15, 1997 [DE] Germany .......................... 197 01 037

[51] Int. Cl.⁶ ..................................... A61K 35/14
[52] U.S. Cl. ........................... 424/529; 514/832
[58] Field of Search .............................. 514/832; 424/529

[56] References Cited

U.S. PATENT DOCUMENTS 5,171,755  12/1992  Kaufman et al. ....................... 514/749

FOREIGN PATENT DOCUMENTS

WO 94/22482  10/1994  WIPO .

OTHER PUBLICATIONS

Ikedo–Saito et al. J. Mol. Biol., 138(4), 845–58 (Abstract), 1980.
Muirhead et al. J. Hypertens., 10(9), 963–7 (Abstract), 1992.

*Primary Examiner*—Raymond Henley, III
*Attorney, Agent, or Firm*—Sprung Kramer Schaefer & Briscoe

[57] ABSTRACT

Artificial oxygen carrier composed of native or modified hemoglobins for direct biological or medical use, in which the oxygen binding site of the hemoglobin is provided with a protective ligand, preferably carbon monoxide, which does not have to be removed prior to use.

9 Claims, No Drawings

HEMOGLOBINS PROVIDED WITH LIGANDS PROTECTING THE OXYGEN BINDING SITES FOR USE AS ARTIFICIAL OXYGEN CARRIERS FOR DIRECT APPLICATION IN MEDICINE AND BIOLOGY, AND METHOD FOR THE PREPARATION THEREOF

The invention relates to artificial oxygen carriers composed of native or modified hemoglobins which are reliably and lastingly protected against loss of function until they are used, which prior to use require no further treatment, and whose reactivation is controllable after use begins, as well as to a method for their preparation.

Artificial oxygen carriers on the basis of hemoglobins are required for many purposes, but during their preparation and storage they can lose their functionality partially or completely. To prevent this it is necessary that artificial hemoglobin oxygen carriers remain usable and capable of storage for as long as possible.

Generally, there are different approaches to the preparation of artificial oxygen carriers; one of them is the preparation of suitable solutions of native or chemically modified hemoglobins (for the state of the research and developments, see "Issues from Vth International Symposium on Blood Substitutes, San Diego, Calif., USA, March 1993", *Artificial Cells, Blood Substitutes, and Immobilization Biotechnology* 22 (1994), vol. 2–vol. 4). One problem in the handling of such pharmaceutical preparations as artificial oxygen carriers is their increasing inactivation by spontaneous oxidation to methemoglobin which can no longer transport oxygen. This applies both to actual manufacture by the producer and to subsequent storage until used.

There are a number of processes and methods for solving this problem. Either they reduce the degree of oxidation of hemoglobin, or the oxidized hemoglobin is reduced back again.

One possibility for an extensive prevention of spontaneous oxidation consists in deoxygenating the hemoglobin (i.e., entirely removing oxygen from the preparation), for desoxyhemoglobin oxidizes much more slowly to methemoglobin than does oxyhemoglobin (ANTONINI et al. (1981) (Editor): *Methods in Enzymolog, Volume 76, Hemoglobin*, Academic Press, New York, et al. 1981). The difficulty of this kind of procedure is the necessity of removing the oxygen really completely, since residual radicals continue to work, and in fact partially oxygenated hemoglobin oxidizes substantially more rapidly than fully oxygenated hemoglobin (BROOKS, J. (1935): "The Oxidation of Haemoglobin to Methaemoglobin by Oxygen, II. The Relation between the Rate of Oxidation and the Partial Pressure of Oxygen", *Proceedings of the Royal Society (London), Series B* 118: 560–570).

Also, on account of the relationship between the oxidation rate and the temperature, it is possible to minimize the amount of oxidation by storage and/or preparation at the lowest possible temperature (for aqueous solutions, at about 4° C.). This, however, necessitates keeping technical apparatus (refrigerators) permanently on hand, and has the additional disadvantage that the preparation has to be warmed prior to its use.

Furthermore, the rate of oxidation of hemoglobin depends on the hydrogen ion concentration, i.e., the pH. For example, for native human hemoglobin there is a minimum in the interval between pH 7.5 and 9.5 (SUGAWARA Y. et al. (1993): "Auto-oxidation of Human Hemoglobin: Kinetic Analysis of the pH Profile," *Japanese Journal of Physiology* 43: 21–34). Measurements on some polymers of human hemoglobin (so-called "hyperpolymers") have shown that this applies also to the latter. Restoration of the pH prior to use is, however, problematic.

Also, the addition of certain alcohols can diminish the oxidation of hemoglobin (NEDJARARROUME N. et al. (1933): "Stabilizing Effect of Water Alcohol Solvents Towards Autooxidation of Human Haemoglobin," *Biotechnology and Applied Biochemistry* 18: 25–36). Some of them work even in low concentration. One problem is the toxicity of these alcohols.

Certain metal ions ($Cu_2+$, $Fe_3+$ etc.) catalyze the spontaneous oxidation of hemoglobin. They can be rendered ineffective by complexation with EDTA (ethylenediaminetetraacetic acid), although EDTA itself promotes the spontaneous oxidation of hemoglobin.

Specific possibilities for the protection of artificial oxygen carriers against oxidation consist in the addition of reducing substances. Under certain circumstances they even produce a reactivation of oxidized hemoglobin.

Firstly, chemical reduction is possible. Reactivation, however, requires transposition with a strong reducing agent (e.g., dithionite: BAUER and PACYNA (1975): "The Conversion of Trivalent to Divalent Iron in Hemoglobin of Various Species," *Analytical Biochemistry* 65: 445–448). If a reducing agent is removed after the reaction, the problem of the oxidation of the hemoglobin again presents itself. If a reducing agent is permanently added, it is applied with the hemoglobin, which greatly limits the choice of appropriate substances. Ascorbic acid might be suitable, for example (TOMODA (1978): "Mechanism of Methemoglobin Reduction by Ascorbic Acid under Anaerobic Conditions," *Journal of Biological Chemistry* 253: 7420–7423). However, it is only a relatively weak reducing agent and thus suitable only for preventing further oxidation.

Hemoglobin can also be reduced enzymatically. A number of possibilities for suitable enzymes and substrates have been described for analytical purposes (HAYASHI et al. (1973): "An Enzymic Reduction System for Metmyoglobin and Methemoglobin, and its Application to Functional Studies of Oxygen Carrier," *Biochimica et Biophysica Acta* 310: 309–316, and ROSSI-FANELLI and ANTONINI (1958): "Studies on the Oxygen and Carbon Monoxide Equilibria of Human Myoglobin," *Archives of Biochemistry and Biophysics* 77: 478–492). The concomitant application of these proteins is problematical, so that with this method all that can be accomplished is protection against oxidation only during the preparation of the artificial oxygen carriers.

A method long known for all steps of the preparation of hemoglobins for the purpose of minimizing the degree of their oxidation is to ligandize them with carbon monoxide, that is, convert them to carbonylhemoglobin (or carboxyhemoglobin). However, this method has never yet been foreseen for the protection of preparations of artificial oxygen carriers intended for use, because a number of arguments appear to prohibit use for the stated purpose: carbon monoxide is bound as a ligand considerably more tightly than oxygen is to the oxygen binding site of the hemoglobin. Therefore, carbonylhemoglobin is virtually unavailable for carrying oxygen. For the physician, therefore, carbonylhemoglobin is "poisoned" hemoglobin, since the fraction of the hemoglobin that is in the form of carbonylhemoglobin is insufficient for oxygen transport. In the case of severe carbon monoxide poisoning, frequently an acute danger to the patient's life is involved and the blocking of the oxygen transport function has to be treated. In experimental work to prove the effectiveness and action of artificial oxygen carriers obtained from hemoglobins, the corresponding hemoglobins ligandized with carbon monoxide are used even as acutely nonfunctional "carriers" (e.g., CONOVER et al. (1996): "Evaluation of the Oxygen Delivery Ability of PEG Hemoglobin in Sprague-Dawley Rats During Hemodilution" (Abstract), *Artificial Cells, Blood Substitutes, and Immobilization Biotechnology* 24: 325). Consequently, any permanent ligandizing of artificial hemoglobin oxygen carriers with carbon monoxide to protect against oxidation does not appear to be practicable.

The invention is addressed to the problem of preserving to the greatest possible extent the functionality of artificial oxygen carriers made from hemoglobins during their preparation and subsequent storage until their use, without the need for any further treatment prior to their use.

This problem is solved by providing the oxygen binding site with a suitable protective ligand. Surprisingly it was found that it is unnecessary to convert the artificial oxygen carrier according to the invention to a form free of protective ligands prior to its biological/medical use.

The stated problem is preferably solved according to the invention by converting the hemoglobin entirely to carbonylhemoglobin and storing it in this form and also using it even thus as an artificial oxygen carrier without further treatment. The protection is accomplished by a ligandization with carbon monoxide performed early on, if desired, in the course of the synthesis (carboxyhemoglobin or carbonylhemoglobin is formed), which, as an essential feature of the invention, is not reversed prior to any use. Instead, the artificial oxygen carrier is used in this form.

The removal of the ligand prior to an application, which is extremely complicated and cannot be performed quickly, can be omitted according to the invention for the following reasons:

1. In the system of blood vessels of an organism or excized organs or in technical apparatus for the culture of cells, the applied carbon monoxide-hemoglobin complex breaks up, according to the hemoglobin-carbon monoxide binding curve, due to the very low partial pressure of the carbon monoxide in the blood plasma or in the nutrient solution. The freed carbon monoxide is exhaled or is removed with the gas supply being exhausted. The hemoglobin incapable of directly transporting oxygen is thus activated by deligandization.
2. In the case of use in an organism, freely dissolved carbon monoxide not bound to hemoglobin in the pharmaceutical preparation of carboxyhemoglobin, which is used simultaneously, was basically capable of forming carboxyhemoglobin with the recipient's own hemoglobin. But by the appropriate selection of the partial pressure of the carbon monoxide its quantity can be kept negligibly low. The hemoglobin-carbon monoxide binding curve permits a complete reaction of the artificial oxygen carrier composed of hemoglobins to the carbonylated form (to carboxyhemoglobin) even at very low partial pressures. Carbon monoxide is a naturally occurring gas.

It was furthermore found that an artificial oxygen carrier protected according to the invention is characterized after administration by a gradual activation, the speed of the reactivation being controllable—within certain limits—by varying the amount of oxygen inhaled by volume or varying the partial pressure of the oxygen.

Carboxyhemoglobin is known to be extremely stable against spontaneous oxidation, even during storage at room temperature, so that, as an achievable advantage, the preparations according to the invention can be stored over a long time without untoward consequences for their function as artificial oxygen carriers.

Moreover, the process of degradation of the hemoglobin-carbon monoxide complexes of the artificial oxygen carrier in the blood can be promoted by increasing the oxygen content of the inhalant gas (increasing the inhaled oxygen portion by volume), as used for therapy, e.g., even including carbon monoxide poisoning, and controlling the speed of the process by the amount of the increase of the oxygen portion of the inhalant gas.

Another important advantage of the use of hemoglobins, protected according to the invention against loss of functionality, as artificial oxygen carriers is to be seen in the possibility—adapted to the requirements of the individual patient or of the special application—of gradually releasing their operation. After therapeutic administration in an organism, no transitory relative oversupply of oxygen occurs in less blood-perfused organs; the tissue, functionally adapted to hypoxia, is thus preserved against oxidative shock by toxic oxygen damage (so-called "reperfusion damage").

An advantageous way to prepare an artificial oxygen carrier composed of hemoglobins pursuant to the invention is to balance them, as early as possible in the course of their manufacture, with carbon monoxide in at least sufficient concentration, e.g., with pure carbon monoxide at first, and thus convert them as completely as possible to carboxyhemoglobin. In this way the hemoglobin used is securely protected even against partial oxidation. This condition is sustained as preparation proceeds. Then, as the final step, in order to minimize the content of freely dissolved carbon monoxide and at the same time obtain the complete ligandization of the hemoglobin with carbon monoxide, balancing it with carbon monoxide of the lowest possible concentration (e.g., with one part by volume of carbon monoxide and 99 parts by volume of nitrogen) and packing the preparation hermetically in this state (e.g., in glass ampules or infusion bottles) for storage and subsequent application.

As ligands for protecting the oxygen binding sites of hemoglobin other groups of substances can be used, as described in the literature (ANTONINI E. et al. (Editor.) (1981); *Methods in Enzymolog Volume 76—Hemoglobins*. A protective ligand which is gaseous in pure form and, like carbon monoxide, suitable for the oxygen binding site, is nitrogen monoxide (NO). Non-gaseous competitive ligands that can be used are "derivatives" of nitrogen monoxide, such as nitroso compounds, and isocyanides, always in the form of certain suitable compounds. Their suitability as protective ligands for such artificial oxygen carriers composed of hemoglobins, which is known to the expert, or easily discovered or determined by simple experiment, depends on their affinity for the oxygen binding site as well as their tolerability by the human organism or the cell culture or preparation that is to be treated.

The selection of particular protective ligands can be geared to the results desired from their use. For example, it is possible by the simultaneous use of different protective ligands with different affinities for hemoglobin to achieve during their use a controlled (graded) activation of the artificial oxygen carrier.

We claim:

1. A method of providing a biological system with oxygen comprising introducing into said biological system a storage-stable hemoglobin-based artificial oxygen carrier comprised of hemoglobin having oxygen binding sites wherein said oxygen binding sites are provided with a carbon monoxide ligand.

2. The method according to claim 1 wherein said hemoglobin is native or chemically modified hemoglobin of human or animal origin.

3. The method according to claim 1 wherein said biological systems are mammals, including human beings.

4. The method according to claim 1 wherein said biological systems are organs, excised for transplantation.

5. The method according to claim 1 wherein said biological systems are devices for cell and microorganism culture and breed.

6. The method according to claim 1 wherein said introduction of the hemoglobin-based artificial oxygen carrier into said biological systems are for diagnostic or therapeutic applications.

7. The method according to claim 3 wherein said biological systems are devices for cell and microorganism culture and breed.

8. The method according to claim 1 wherein said biological systems are utilized for diagnostic applications.

9. A method of regulating the rate of reactivation of carbon monoxide ligandized hemoglobin based artificial oxygen carriers which comprises applying said oxygen carriers to a biological system receiving a supporting gas or a breathing gas wherein said artificial oxygen carrier is comprised of hemoglobin having oxygen binding sites wherein said oxygen binding sites are occupied with a carbon monoxide ligand wherein the oxygen content of said supporting gas or said breathing gas of said biological system is varied.

* * * * *